(12) United States Patent
Nagai et al.

(10) Patent No.: US 11,346,841 B2
(45) Date of Patent: May 31, 2022

(54) SPECIMEN MEASUREMENT SYSTEM AND SPECIMEN MEASUREMENT METHOD

(71) Applicant: SYSMEX CORPORATION, Kobe (JP)

(72) Inventors: Takaaki Nagai, Kobe (JP); Hideki Hirayama, Kobe (JP); Hiroo Tatsutani, Kobe (JP); Tomohiro Tsuji, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 328 days.

(21) Appl. No.: 16/579,989

(22) Filed: Sep. 24, 2019

(65) Prior Publication Data

US 2020/0096515 A1 Mar. 26, 2020

(30) Foreign Application Priority Data

Sep. 26, 2018 (JP) .............................. JP2018-180907

(51) Int. Cl.
*G01N 33/574* (2006.01)
*G01N 15/14* (2006.01)
(Continued)

(52) U.S. Cl.
CPC ....... *G01N 33/57426* (2013.01); *G01N 15/14* (2013.01); *G01N 21/6428* (2013.01);
(Continued)

(58) Field of Classification Search
CPC ............... G01N 15/14; G01N 15/1459; G01N 2015/1006; G01N 2021/6439; G01N 21/6428; G01N 33/5094; G01N 33/57426; G01N 35/0092; G01N 35/02; G06K 9/00127; G06T 2207/30024; G06T 7/0012

See application file for complete search history.

(56) References Cited

U.S. PATENT DOCUMENTS 5,554,505 A * 9/1996 Hajek .................... G01N 1/312
435/7.21
6,300,088 B1 * 10/2001 Enghild ............... C12N 9/6445
435/4

(Continued)

FOREIGN PATENT DOCUMENTS

EP 3 410 094 A1 12/2018
JP 2011214835 A 10/2011
(Continued)

OTHER PUBLICATIONS

Extended European Search Report dated Feb. 19, 2020, by the European Patent Office in corresponding European Patent Application No. 19199217.1. (9 pages).

(Continued)

*Primary Examiner* — Jennifer Wecker
*Assistant Examiner* — Jonathan Bortoli
(74) *Attorney, Agent, or Firm* — Buchanan Ingersoll & Rooney PC

(57) ABSTRACT

Disclosed is a specimen measurement system including: a specimen measuring device that measures a specimen; a determination unit that determines whether or not the specimen is to be measured by a flow cytometer, based on a measurement result of the specimen measuring device.

22 Claims, 9 Drawing Sheets

(51) Int. Cl.
  *G01N 21/64*   (2006.01)
  *G06T 7/00*    (2017.01)
  *G06V 20/69*   (2022.01)

(52) U.S. Cl.
  CPC ............ *G06T 7/0012* (2013.01); *G06V 20/69* (2022.01); *G01N 2021/6439* (2013.01); *G06T 2207/30024* (2013.01)

(56) References Cited

U.S. PATENT DOCUMENTS

| | | |
|---|---|---|
| 9,222,952 B2 | 12/2015 | Tatsutani et al. |
| 2010/0228491 A1 | 9/2010 | Gutierrez et al. |
| 2011/0243792 A1 | 10/2011 | Tatsutani et al. |
| 2013/0065317 A1* | 3/2013 | Fukuma ............ G01N 33/4915 436/63 |
| 2013/0317773 A1* | 11/2013 | Oda ................ G01N 35/00603 702/104 |
| 2017/0315047 A1 | 11/2017 | Yamada |
| 2018/0017480 A1 | 1/2018 | Fukuda et al. |

FOREIGN PATENT DOCUMENTS

| | | |
|---|---|---|
| JP | 2017198625 A | 11/2017 |
| WO | 92/09878 A1 | 6/1992 |
| WO | 2016157982 A1 | 10/2016 |

OTHER PUBLICATIONS

Communication pursuant to Article 94(3) EPC dated Apr. 13, 2021, by the European Patent Office in corresponding European Patent Application No. 19199217.1. (8 pages).

\* cited by examiner

DO YOU PREPARE A SAMPLE BASED ON SET MEASUREMENT ITEMS?

YES    RESET OF MEASUREMENT ITEMS

| SPECIMEN NUMBER | MEASUREMENT ITEM 1 | MEASUREMENT ITEM 2 | MEASUREMENT ITEM 3 | MEASUREMENT ITEM 4 |
|---|---|---|---|---|
| 123456789 | CD34 | CD45 | NOT SET | NOT SET |

OK

SPECIMEN MEASUREMENT SYSTEM AND SPECIMEN MEASUREMENT METHOD

CROSS REFERENCE TO RELATED APPLICATIONS

This application claims priority from prior Japanese Patent Application No. 2018-180907, filed on Sep. 26, 2018, entitled "Specimen measurement system and specimen measurement method", the entire contents of which are incorporated herein by reference.

TECHNICAL FIELD

The present invention relates to an inspection technology, and relates to a specimen measurement system and a specimen measurement method.

BACKGROUND

At medical sites such as hospitals and examination centers, a large number of specimens are tested. Each specimen is measured using a plurality of measuring devices. For example, when a medical worker determines that there is a possibility of disease by measuring the specimen with a measuring device, a more detailed test is done to determine whether the specimen has a feature that appears in individual disease, using another measuring device with higher accuracy.

For example, it has been proposed to measure a blood specimen with a blood measuring device, prepare a smear preparation from the blood specimen based on a measurement result of the blood measuring device, and analyze an image of the smear specimen (see, for example, U.S. Pat. No. 9,222,952). When inspecting for human T cell leukemia virus (HTLV) infection, sometimes, a blood specimen that has reacted with an anti-HTLV antibody and a labeled antibody is measured with a spectroscope, and further, the blood specimen is measured by a flow cytometer.

When the specimen is pretreated with a labeling reagent such as an antibody reagent to prepare a sample and the sample is analyzed by a flow cytometer, it is possible to examine the possibility of disease in more detail. A pretreatment device of the flow cytometer described in US 2017/0315,047 A reads a bar code recording a specimen ID, which is attached to a container containing a specimen to be pretreated, with a reader, and accesses an external management computer. The pretreatment device acquires measurement item information of the flow cytometer for the specimen from the management computer, mixes the specimen and the labeling reagent based on the measurement item information, and prepares a sample. In addition, the pretreatment device centrifuges the sample as necessary.

Among specimens measured by a primary measuring device, specimens that are pretreated with a labeling reagent and further measured by a flow cytometer in detail are a part of the whole. In the presence of a large number of specimens, it is complicated and difficult for a medical worker to manage and identify specimens for which more detailed measurements are required. In addition, when extracting a specimen for which more detailed measurement is required, there is a risk that a wrong specimen is extracted or the extracted specimen is transported to a wrong measuring device.

SUMMARY OF THE INVENTION

The scope of the present invention is defined solely by the appended claims, and is not affected to any degree by the statements within this summary.

According to an aspect of the present invention, there is provided a specimen measurement system including a specimen measuring device 10 that measures a specimen, and a determination unit 301 that determines whether or not the specimen is to be measured by a flow cytometer, based on a measurement result of the specimen measuring device 10. The determination unit 301 is included in a computer or the like.

According to the specimen measurement system, it is possible to identify the specimen that needs to be measured by a flow cytometer, among the specimens measured by the specimen measuring device 10, based on the measurement result of the specimen measuring device 10.

In the specimen measurement system, when the measurement result of the specimen matches a predetermined condition, the determination unit 301 may determine that the specimen is to be measured by the flow cytometer. The predetermined condition may be set in advance based on, for example, a criterion of disease possibility.

According to the specimen measurement system, it is possible to identify a specimen in which a subject that has provided the specimen may have a disease, as a specimen that needs to be measured by a flow cytometer.

In the specimen measurement system, the specimen measuring device 10 may include a flow cytometer that is separate from the above flow cytometer.

According to the specimen measurement system, it is possible to measure the specimen stepwise by a plurality of flow cytometers.

In the specimen measurement system, a specimen to be measured by the specimen measuring device 10 may not be treated with a labeling reagent containing an antibody.

According to the specimen measurement system, it is possible to suppress use of expensive labeling reagent.

In the specimen measurement system, the specimen is a blood specimen, the specimen measuring device 10 includes a blood cell measuring apparatus that measures blood cells contained in the blood specimen, and the determination unit 301 may determine whether or not the specimen is to be measured by a flow cytometer, based on a measurement result of the blood cell measuring apparatus. The blood cells may be at least one of leukocytes including blasts, lymphocytes and the like, erythrocytes and platelets. In at least any of the cases where blasts are present, the number of lymphocytes meets a predetermined criterion, the number of erythrocytes meets a predetermined criterion, and the number of platelets meets a predetermined criterion, the determination unit 301 may determine that the specimen is to be measured by the flow cytometer.

According to the specimen measurement system, it is possible to identify a blood specimen that needs to be measured by the flow cytometer, based on the state of blood cells contained in the blood specimen.

The specimen measurement system further includes an image analysis apparatus 330 that analyzes an image of a preparation smeared with a blood specimen in addition to the specimen measuring device 10, and the determination unit 301 may determine whether or not the specimen is to be measured by the flow cytometer, further based on an analysis result of the image analysis apparatus 330. Alternatively, in the specimen measurement system, the specimen is a blood specimen, and the specimen measuring device 10 includes an image analysis apparatus that analyzes an image of a preparation smeared with the blood specimen, and the determination unit 301 may determine whether or not the specimen is to be measured by the flow cytometer, based on an analysis result of the image analysis apparatus. The image analysis apparatus 330 may analyze whether the image of the preparation includes leukemia cells, and when the image of the preparation includes leukemia cells, the determination unit 301 may determine that the specimen is to be measured by the flow cytometer. The specimen measurement system may further include a smear preparing apparatus 61 that prepares a preparation smeared with a blood specimen.

According to the specimen measurement system, it is possible to identify a blood specimen that needs to be measured by the flow cytometer, based on the smear preparation of the blood specimen.

In the specimen measurement system, blood specimens may be derived from the same subject at different times. The determination unit 301 may determine whether or not the specimen is to be measured by the flow cytometer, based on a change in the number of blood cells contained in a blood specimen derived from the same subject at different times.

According to the specimen measurement system, it is possible to identify a blood specimen that needs to be measured by the flow cytometer, based on the smear preparation of the blood specimen derived from the same subject.

The specimen measurement system may further include a measurement order generating unit 302 that generates a measurement order for the flow cytometer, based on the measurement result of the specimen measuring device 10.

Alternatively, the specimen measurement system may further include a measurement order generating unit 302 that generates a measurement order for the flow cytometer, based on the measurement result of the specimen measuring device 10 and the analysis result of the image analysis apparatus 330.

According to the specimen measurement system, it is possible to automatically generate the measurement order for the flow cytometer, based on the measurement result of the specimen measuring device 10 or the measurement result of the specimen measuring device 10 and the analysis result of the image analysis apparatus 330.

In the specimen measurement system, in the measurement order, a labeling reagent for preparing a sample from the specimen may be designated. The specimen measurement system may further include a sample preparation device 30 that prepares a sample to be measured by the flow cytometer, at least from a labeling reagent and the specimen, and the sample preparation device 30 may prepare the sample based on the measurement order.

According to the specimen measurement system, it is possible to automatically designate a labeling reagent for preparing a sample from the specimen, and the sample preparation device 30 can automatically prepare a sample.

When the specimen measurement system may further include a specimen transport device 40 that transports the specimen to the sample preparation device 30 when the determination unit 301 determines that the specimen is to be measured by the flow cytometer. In the specimen measurement system, the specimen transport device 40 may transport a specimen container containing the specimen.

According to the specimen measurement system, it is possible to automatically transport the specimen determined by the determination unit 301 to be measured by the flow cytometer to the sample preparation device 30.

The specimen measurement system may further include a storage unit 70 for storing a specimen container. The storage unit 70 may be disposed between the specimen measuring device 10 and the sample preparation device 30. The storage unit 70 may store the specimen container until the sample preparation device 30 can prepare a sample from the specimen.

According to the specimen measurement system, it is possible to stand by keeping the specimen in the container until the sample preparation device 30 can prepare a sample from the specimen.

In the specimen measurement system, the specimen transport device 40 may transport the specimen using a specimen rack capable of holding a plurality of specimen containers.

According to the specimen measurement system, the specimen transport device 40 can automatically transport a plurality of specimens that need to be measured by the flow cytometer to the sample preparation device 30, among the specimens measured by the specimen measuring device 10, based on the measurement result of the specimen measuring device 10.

The specimen measurement system may further include a specimen transfer device 80 that transfers the specimen container held in the specimen rack to another specimen rack, according to the destination of the specimen.

According to the specimen measurement system, it is possible to transfer the specimen container held in the specimen rack to another specimen rack according to the destination of the specimen.

The specimen measurement system may further include a placement unit 50 on which the specimen is placed, and the specimen transport device 40 may transport the specimen from the placement unit 50 to the specimen measuring device 10. The specimen transport device 40 may return the specimen not transported to the sample preparation device 30 to the placement unit 50.

According to the specimen measurement system, it is possible to prevent retention of the specimen which does not need to be transported to the sample preparation device 30.

The specimen measurement system may further include a sample transport device that transports the sample prepared by the sample preparation device to the sample measuring device. The sample transport device may transport a sample container containing a sample from the sample preparation device 30 to the flow cytometer.

According to the specimen measurement system, the sample transport device can automatically transport a specimen that needs to be measured by the flow cytometer, to the flow cytometer among the specimens measured by the specimen measuring device 10, based on the measurement result of the specimen measuring device 10.

Further, according to an aspect of the present invention, there is provided a specimen measurement method, in which a specimen measuring device 10 measures a specimen, and a determination unit 301 determines whether or not the specimen is to be measured by a flow cytometer, based on a measurement result of the specimen measuring device 10.

According to the specimen measurement method, it is possible to identify the specimen that needs to be measured by the flow cytometer, among the specimens measured by the specimen measuring device 10, based on the measurement result of the specimen measuring device 10.

In the specimen measurement method, in the determination, when the measurement result of the specimen matches a predetermined condition, the determination unit 301 may determine that the specimen is to be measured by the flow cytometer.

The predetermined condition may be set in advance based on, for example, a criterion of disease possibility.

According to the specimen measurement method, it is possible to identify a specimen in which a subject that has provided the specimen may have a disease, as a specimen that needs to be measured by the flow cytometer.

In the specimen measurement method, in the measurement, the specimen may be measured by the flow cytometer separate from the flow cytometer.

According to the specimen measurement method, it is possible to measure the specimen stepwise by a plurality of flow cytometers.

In the specimen measurement method, the specimen to be measured by the specimen measuring device 10 may not be treated with a labeling reagent containing an antibody.

According to the specimen measurement method, it is possible to suppress use of expensive labeling reagent.

In the specimen measurement method, the specimen is a blood specimen, in the measurement, a blood cell measuring apparatus included in the specimen measuring device 10 measures blood cells contained in the blood specimen, and in the determination, the determination unit 301 determines whether or not the specimen is to be measured by the flow cytometer, based on a measurement result of the blood cell measuring apparatus. The blood cells are at least one of leukocytes including blasts and lymphocytes, erythrocytes and platelets, and in any of the cases where blasts are present, the number of lymphocytes meets a predetermined criterion, the number of erythrocytes meets a predetermined criterion, and the number of platelets meets a predetermined criterion, and in the determination, the determination unit 301 determines that the specimen is to be measured by the flow cytometer.

According to the specimen measurement method, it is possible to identify a blood specimen that needs to be measured by the flow cytometer, based on the state of blood cells contained in the blood specimen.

In addition to that the specimen measurement method in which the blood cell measuring apparatus included in the specimen measuring device 10 measures blood cells contained in the blood specimen, in that the image analysis apparatus 330 analyzes an image of a preparation smeared with the blood specimen, and in the determination, the determination unit 301 may determine whether or not the specimen is to be measured by the flow cytometer, further based on an analysis result of the image of the preparation. Alternatively, in the specimen measurement method, the specimen is a blood specimen, in the measurement, the image analysis apparatus included in the specimen measuring device 10 analyzes an image of a preparation smeared with the blood specimen, and in the determination, the determination unit 301 may determine whether or not the specimen is to be measured by the flow cytometer, based on an analysis result of the image analysis apparatus. In analyzing the image of the preparation, it is analyzed whether the image of the preparation includes leukemia cells, and when the image of the preparation includes leukemia cells, in the determination, the determination unit 301 may determine that the specimen is to be measured by the flow cytometer. In the specimen measurement method, the smear preparing apparatus 61 may prepare a preparation smeared with the blood specimen.

According to the specimen measurement method, it is possible to identify a blood specimen that needs to be measured by the flow cytometer, based on a smear preparation of the blood specimen.

In the specimen measurement method, the determination unit 301 may determine whether or not the specimen is to be measured by the flow cytometer, based on a change in the number of blood cells contained in a blood specimen derived from the same subject at different times.

According to the specimen measurement method, it is possible to identify a blood specimen that needs to be measured by the flow cytometer, based on the smear preparation of the blood specimen derived from the same subject.

In the specimen measurement method, the measurement order generating unit 302 may generate a measurement order for the flow cytometer, based on the measurement result of the specimen measuring device 10. Alternatively, in the specimen measurement method, the measurement order generating unit 302 may generate a measurement order for the flow cytometer, based on the measurement result of the specimen measuring device 10 and the analysis result of the image of the preparation.

According to the specimen measurement method, it is possible to automatically generate the measurement order of a sample to be prepared from the specimen, based on the measurement result of the specimen measuring device 10 or the measurement result of the specimen measuring device 10 and the analysis result of the image analysis apparatus 330.

In the specimen measurement method, in the measurement order, a labeling reagent for preparing a sample to be measured by the flow cytometer from the specimen may be designated. In the preparation, the sample preparation device 30 may prepare a sample to be measured by the flow cytometer based on the measurement order.

According to the specimen measurement method, it is possible to designate a labeling reagent for preparing a sample to be measured by the flow cytometer from the specimen, and the sample preparation device 30 can prepare a sample.

According to the present invention, it is possible to provide a specimen measurement system and a specimen measurement method capable of identifying a specimen that needs to be further examined by a flow cytometer, among specimens examined by a primary test device.

DETAILED DESCRIPTION OF THE PREFERRED EMBODIMENTS

Hereinafter, embodiments of the present disclosure will be described with reference to the drawings. In the following description of the drawings, the same or similar parts are denoted by the same or similar symbols. However, the drawings are schematic. Therefore, specific dimensions and the like should be determined in light of the following description. It is a matter of course that parts having different dimensional relationships and ratios are included also among the drawings.

Figure 1:
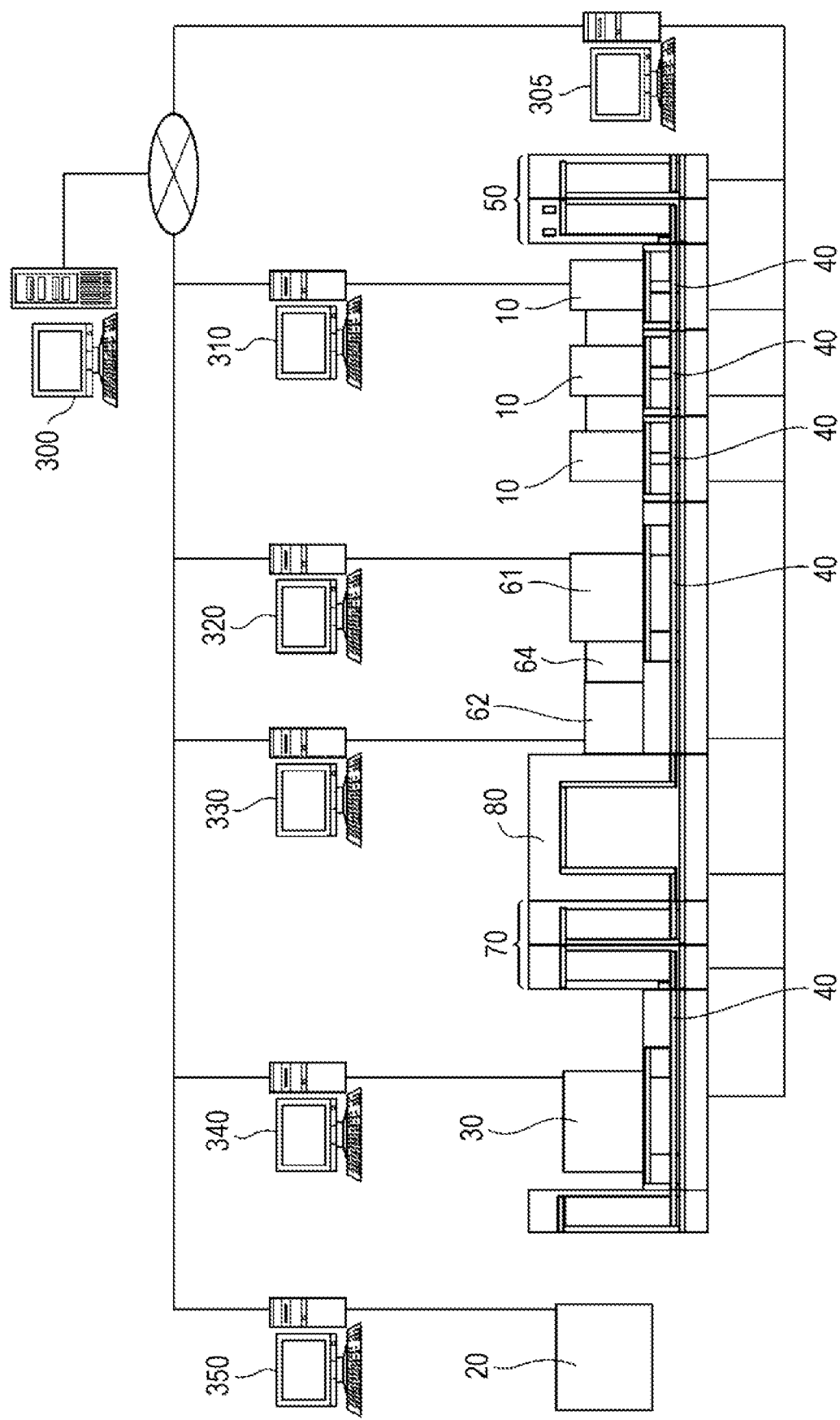
FIG. 1 is a schematic top view of a specimen measurement system according to an embodiment.

The embodiments shown below are examples in which the present disclosure is applied to hematopoietic tumor test. The specimen measurement system according to the embodiment includes, as shown in FIG. 1, a specimen measuring device 10 that measures a specimen, and a host computer 300 including a determination unit that determines whether or not the specimen is to be measured by a flow cytometer, based on a measurement result of the specimen measuring device 10. The specimen measurement system according to the embodiment may include a plurality of specimen measuring devices 10. In FIG. 1, a flow cytometer is included in the sample measuring device 20.

Figure 2A:
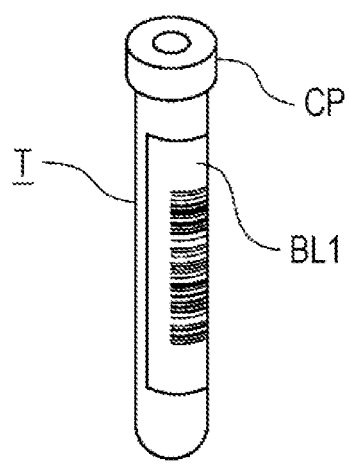
FIGS. 2A and 2B are a schematic view showing a specimen container and a specimen rack according to the embodiment.
Figure 2B:
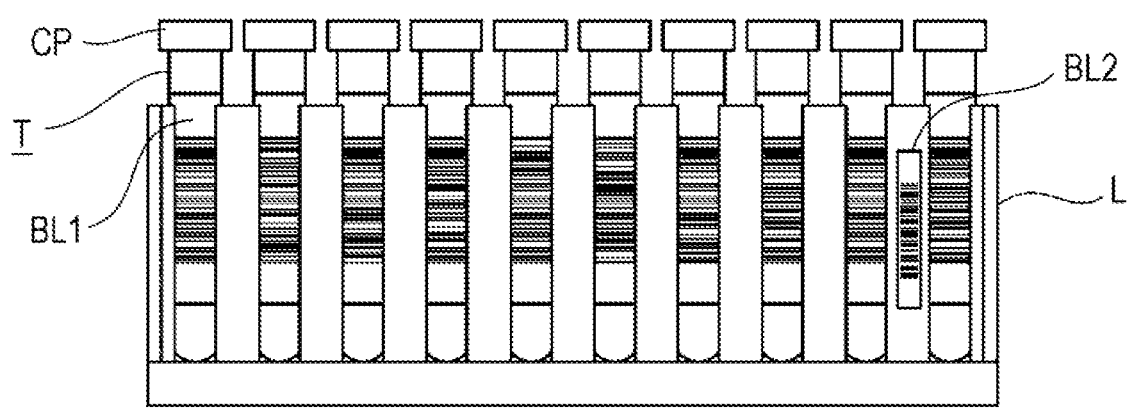

The specimen is a blood specimen such as peripheral blood. The specimen may be a body fluid including bone marrow fluid, lymph node suspension, pleural effusion, ascites fluid, or the like. Hereinafter, an example in which the specimen is a blood specimen will be described. As shown in FIG. 2A, the specimen is contained in a specimen container T such as a test tube. An opening of the specimen container is sealed with a stopper CP made of rubber or the like. As shown in FIG. 2B, one or more specimen containers T may be held by a specimen rack L. Each of the specimen container T and the specimen rack L is provided with identifiers BL1 and BL2 such as barcodes.

The specimen measurement system according to the embodiment includes, as shown in FIG. 1, a placement unit 50 on which a specimen rack holding a plurality of specimen containers is placed. The placement unit 50 includes a reader that reads an identifier. The reader included in the placement unit 50 reads the identifier of the specimen container and the identifier of the specimen rack. The reader sends the read identifier to a transport controller 305.

The transport controller 305 queries the host computer 300 via a communication network whether the received identifier corresponds to a specimen to be examined by any of the plurality of specimen measuring devices 10. When the received identifier corresponds to the specimen to be examined by any of the plurality of specimen measuring devices 10, the transport controller 305 controls the placement unit 50, and the placement unit 50 sends out the specimen rack containing the specimen container to the specimen transport device 40. Further, the transport controller 305 controls the specimen transport device 40, and the specimen transport device 40 transports the specimen rack holding the specimen container from the placement unit 50 to the specimen measuring device 10 designated by the transport controller 305. The specimen transport device 40 includes a conveyor.

Each of the plurality of specimen measuring devices 10 includes a reader that reads an identifier. The reader included in each of the plurality of specimen measuring devices 10 reads the identifier of the specimen container and the identifier of the specimen rack. The reader sends the read identifier to an information processing unit 310. The information processing unit 310 queries the host computer 300 via the communication network for a measurement order prepared in advance for the identifier. The information processing unit 310 sends the measurement order received from the host computer 300 to each of the plurality of specimen measuring devices 10. However, a medical worker may carry the specimen to each of the plurality of specimen measuring devices 10.

For example, each of the plurality of specimen measuring devices 10 pierces a stopper of the specimen container with a suction tube, aspirates a required amount of specimen from the specimen container, and measures the specimen according to the measurement order transmitted from the host computer 300. Each of the plurality of specimen measuring devices 10 includes a blood cell measuring apparatus that measures blood cells contained in a blood specimen. Examples of blood cells include leukocytes including blasts, lymphocytes and the like, erythrocytes and platelets and the like. In general, blasts are sometimes referred to as leukemia cells because there are no blasts in the peripheral blood of healthy individuals and are blasts in the peripheral blood of acute leukemia patients. The blood cell measuring apparatus may measure hemoglobin concentration.

A flow cytometer can be used as the blood cell measuring apparatus. However, the flow cytometer included in the specimen measuring device 10 is a device separate from the flow cytometer included in the sample measuring device 20. When measuring the specimen with a flow cytometer included in the specimen measuring device 10, pretreatment of the specimen with a labeling reagent such as an antibody reagent is not necessarily required. For example, when measuring the specimen with a flow cytometer included in the specimen measuring device 10, the specimen is not treated with a labeling reagent used when preparing a sample by the sample preparation device 30. The labeling reagent used when preparing a sample by the sample preparation device 30 includes, for example, an antibody such as a monoclonal antibody.

Figure 3:
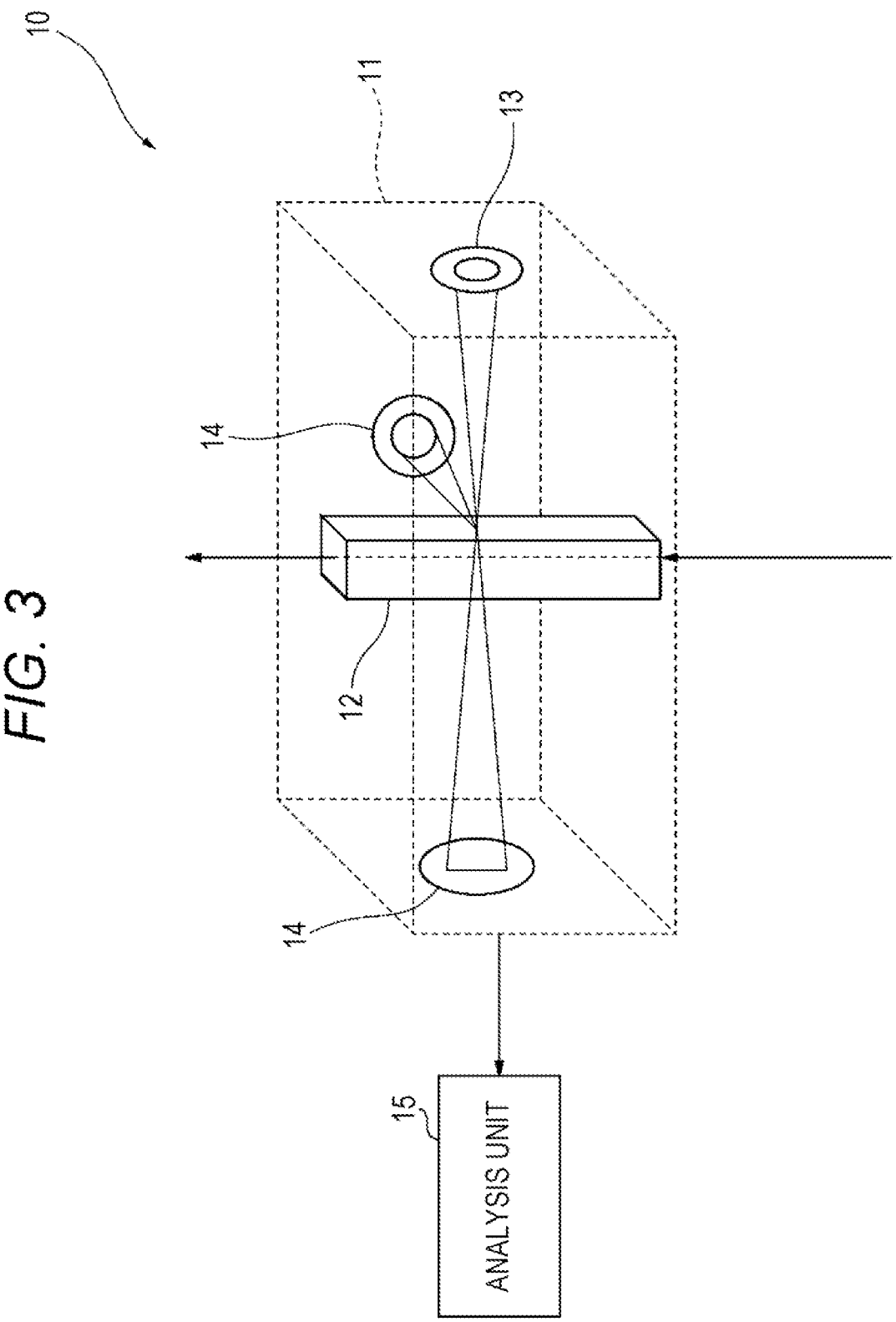
FIG. 3 is a schematic view of a flow cytometer included in a specimen measuring device according to the embodiment.

As shown in FIG. 3, a flow cytometer 11 included in the specimen measuring device 10 includes a flow cell 12. The flow cytometer 11 sends the specimen to the flow cell 12. The specimen supplied to the flow cell 12 is irradiated with light from a light source 13, and a light detection unit 14 detects forward scattered light, side scattered light, and fluorescence emitted from the specimen. An analysis unit 15 is connected to the light detection unit 14. The analysis unit 15 analyzes the forward scattered light, the side scattered light, and the fluorescence detected by the light detection unit 14 to classify the types of blood cells contained in the specimen and measure the blood cells. The analysis unit 15 is included in the information processing unit 310 illustrated in FIG. 1.

Figure 4:
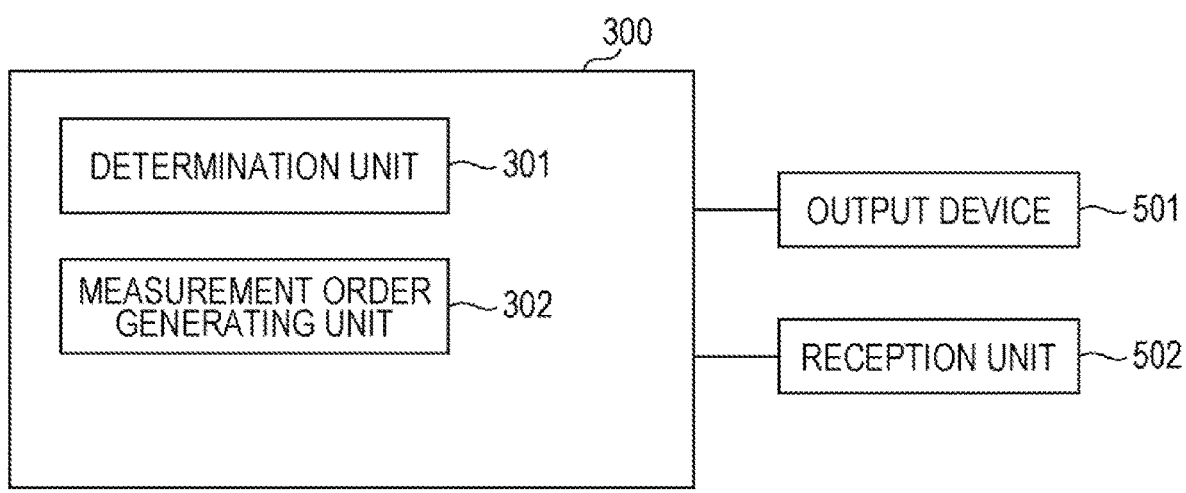
FIG. 4 is a block diagram of a host computer of the specimen measurement system according to the embodiment.

As shown in FIG. 4, the determination unit 301 included in the host computer 300 receives a measurement result of the specimen from the information processing unit 310 connected to the specimen measuring device 10 shown in FIG. 1.

The measurement result of the specimen is a flag indicating the possibility of the presence of blasts, counting results of leukocytes including lymphocytes, erythrocytes and platelets and the like, and hemoglobin concentration. The determination unit 301 determines whether or not the specimen is to be measured by the flow cytometer included in the sample measuring device 20, based on the measurement result of the specimen by the specimen measuring device 10. For example, the determination unit 301 determines whether the specimen meets a predetermined condition. The determination unit 301 may determine whether the specimen meets the predetermined condition, based on a change in the number of blood cells contained in a blood specimen derived from the same subject at different times. The predetermined condition is set in advance based on, for example, a criterion of disease possibility.

The specimen measurement system according to the embodiment further includes a smear preparing apparatus 61 that prepares a preparation smeared with a blood specimen. When the specimen meets the predetermined condition, the determination unit 301 determines that the specimen is to be measured by the flow cytometer included in the sample measuring device 20. For example, in this case, the determination unit 301 determines that the specimen is to be transported to the smear preparing apparatus 61 or the sample preparation device 30 by the specimen transport device 40. The determination unit 301 may determine that the specimen is to be transported to the sample preparation device 30 without interposing the smear preparing apparatus 61, based on the measurement result of the specimen by the specimen measuring device 10. When the specimen does not meet the predetermined condition in the measurement result of the specimen, the determination unit 301 determines that the specimen is not to be measured by the flow cytometer included in the sample measuring device 20. For example, in this case, the determination unit 301 determines that the specimen is not to be transported to the smear preparing apparatus 61 and the sample preparation device 30 by the specimen transport device 40.

For example, the determination unit 301 determines whether predetermined criteria such as whether the number of leukocytes is high, whether leukocyte count classification is abnormal, or whether a flag indicating the presence of blasts is set are met. The leukocyte count classification is, for example, the number or abundance of neutrophils, lymphocytes, monocytes, eosinophils and basophils in leukocytes. When the predetermined criteria are met, the subject who provided the specimen may have a hematopoietic tumor. When the predetermined criteria are not met, the possibility that the subject has a hematopoietic tumor is low.

When the subject may have a hematopoietic tumor, the determination unit 301 determines that the specimen is to be measured by the flow cytometer included in the sample measuring device 20. For example, in this case, the determination unit 301 determines that the specimen is to be transported to the smear preparing apparatus 61 or the sample preparation device 30 by the specimen transport device 40. When the possibility that the subject has a hematopoietic tumor is low, the determination unit 301 determines that the specimen is not to be measured by the flow cytometer included in the sample measuring device 20. For example, in this case, the determination unit 301 determines that the specimen is not to be transported to the smear preparing apparatus 61 and the sample preparation device 30 by the specimen transport device 40.

For example, an output device 501 that outputs a determination result of the determination unit 301 is connected to the host computer 300 including the determination unit 301. As the output device 501, a display such as a liquid crystal display and an organic EL display can be used. When the determination unit 301 determines that the specimen is to be measured by the flow cytometer, a medical worker may carry the specimen to the flow cytometer.

When the determination unit 301 determines that the specimen is to be transported to the smear preparing apparatus 61 or the sample preparation device 30 by the specimen transport device 40, the transport controller 305 controls the specimen transport device 40, and the specimen transport device 40 transports the specimen rack holding the specimen container from the specimen measuring device 10 to the smear preparing apparatus 61 or the sample preparation device 30. When the determination unit 301 determines that the specimen is not to be transported to the smear preparing apparatus 61 and the sample preparation device 30 by the specimen transport device 40, the transport controller 305 controls the specimen transport device 40, and the specimen transport device 40 returns the specimen rack holding the specimen container from the specimen measuring device 10 to the placement unit 50.

When the determination unit 301 determines that the specimen is to be transported to the smear preparing apparatus 61 by the specimen transport device 40, the transport controller 305 controls the specimen transport device 40, and the specimen transport device 40 transports the specimen rack holding the specimen container from the specimen measuring device 10 to the smear preparing apparatus 61. The reader included in the smear preparing apparatus 61 reads the identifier of the specimen container and the identifier of the specimen rack. The reader sends the read identifier to an information processing unit 320. The information processing unit 320 queries the host computer 300 via the communication network for whether the specimen provided with the identifier is a target of smear preparation. When the specimen provided with the identifier is the target of smear preparation, for example, the smear preparing apparatus 61 pierces a stopper of the specimen container with a suction tube to aspirate a required amount of specimen from the specimen container. The smear preparing apparatus 61 smears the specimen on a transparent substrate such as a slide glass. The smear preparing apparatus 61 stains the specimen with a staining solution to prepare a smear preparation.

The specimen measurement system according to the embodiment further includes an imaging device 62 that images a smear preparation. A precipitation transport device 64 is disposed between the smear preparing apparatus 61 and the imaging device 62.

The precipitation transport device 64 transports a cassette containing the smear preparation prepared by the smear preparing apparatus 61 from the smear preparing apparatus 61 to the imaging device 62. The imaging device 62 captures an image of a smear preparation using a microscope unit.

The specimen measurement system according to the embodiment further includes an image analysis apparatus 330 that analyzes the image of the smear preparation captured by the imaging device 62. The image analysis apparatus 330 counts blood cells contained in the image of the smear preparation by type. The image analysis apparatus 330 analyzes, for example, whether blasts are included in the image of the smear preparation. When blasts are included in the image of the smear preparation, the image analysis apparatus 330 extracts blasts from the image of the smear preparation and calculates the number or concentration of blasts.

The determination unit 301 of the host computer 300 is connected to the image analysis apparatus 330 via the communication network. The determination unit 301 receives an analysis result of the image of the smear preparation from the image analysis apparatus 330. The analysis result of the image of the smear preparation is the concentration of blasts. The determination unit 301 determines whether the specimen meets a predetermined condition, based on the measurement result of the specimen by the specimen measuring device 10 and the analysis result of the image of the smear preparation by the image analysis apparatus 330. The predetermined criteria indicates that, for example, the measurement result of the specimen by the specimen measuring device 10 indicates that the number of leukocytes is high, the leukocyte count classification is abnormal, and blasts are present, and also refers that the analysis result of the image of the smear preparation indicates that the number or concentration of blasts is equal to or more than a predetermined value. Alternatively, the predetermined criteria indicates that, for example, the measurement result of the specimen by the specimen measuring device 10 indicates abnormal leukocyte scattergram, and also refers that the analysis result of the image of the smear preparation indicates that the number or concentration of blasts is equal to or more than a predetermined value. When the specimen meets the predetermined condition, the determination unit 301 determines that the specimen is to be measured by the flow cytometer included in the sample measuring device 20. For example, in this case, the determination unit 301 determines that the specimen is to be transported to the sample preparation device 30 by the specimen transport device 40. When the specimen does not meet the predetermined condition in the measurement result of the specimen, the determination unit 301 determines that the specimen is not to be measured by the flow cytometer included in the sample measuring device 20. For example, in this case, the determination unit 301 determines the specimen is not to be transported to the sample preparation device 30 by the specimen transport device 40.

When the determination unit 301 determines that the specimen is to be transported to the sample preparation device 30 by the specimen transport device 40, the transport controller 305 controls the specimen transport device 40, and the specimen transport device 40 transports the specimen rack holding the specimen container from the smear preparing apparatus 61 to the sample preparation device 30. When the determination unit 301 determines that the specimen is not to be transported to the sample preparation device 30 by the specimen transport device 40, the transport controller 305 controls the specimen transport device 40, and the specimen transport device 40 returns the specimen rack holding the specimen container from the smear preparing apparatus 61 to the placement unit 50.

The specimen measurement system according to the embodiment further includes a measurement order generating unit 302 shown in FIG. 4 that generates a measurement order of the flow cytometer included in the sample measuring device 20, based on at least one of the measurement result by the specimen measuring device 10 and the analysis result of the image of the smear preparation by the image analysis apparatus 330. The measurement order generating unit 302 is included in the host computer 300.

The measurement result of the specimen by the specimen measuring device 10 indicates that the number of leukocytes is high, the leukocyte count classification is abnormal, and blasts are present, and when the analysis result of the image of the smear preparation indicates that the number or concentration of blasts is equal to or more than a predetermined value, the subject may have acute myeloid leukemia (AML). When the predetermined criteria are met, the measurement order generating unit 302 generates a measurement order that labels the specimen with an antibody panel used for determination of acute myeloid leukemia (AML). Antigens targeted by the antibody panel used for the determination of acute myeloid leukemia (AML) are, for example, CD7, CD11b, CD13, CD14, CD15, CD16, CD33, CD34, CD45, CD56, CD117 and HLA-DR. In this case, since the antibody panel used for determination of acute lymphocytic leukemia (ALL) is not necessary, it is possible to reduce the cost of the labeling reagent used in the measurement by the flow cytometer included in the sample measuring device 20.

When the measurement result of the specimen by the specimen measuring device 10 indicates abnormal leukocyte scattergram, and the analysis result of the image of the smear preparation indicates that the number or concentration of blasts is equal to or more than a predetermined value, the subject may have acute lymphocytic leukemia (ALL). When the predetermined criteria are met, the measurement order generating unit 302 generates a measurement order that labels the specimen with an antibody panel used for the determination of acute lymphocytic leukemia (ALL). Antigens targeted by the antibody panel used for the determination of acute lymphocytic leukemia (ALL) are, for example, CD5, CD10, CD19, CD20, CD45, Igκ, Igλ, CD2, CD3, CD4, CD7, CD8 and CD56. In this case, since the antibody panel used for determination of acute myeloid leukemia (AML) is not necessary, it is possible to reduce the cost of the labeling reagent used in the measurement by the flow cytometer included in the sample measuring device 20.

The measurement order generating unit 302 generates wavelength of excitation light used in the flow cytometer included in the sample measuring device 20, wavelength of fluorescence to be measured, and flow velocity of a fluid flowing through a flow cell, according to a fluorescent reagent contained in the labeling reagent.

Figure 5:
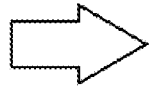
FIG. 5 is a schematic view of an output displayed upon receiving a change in measurement items of a measurement order according to the embodiment.

The output device 501 may output the generated measurement order. In addition, as shown in FIG. 5, the output device 501 may display for querying a medical worker whether the sample may be prepared based on measurement items of the generated measurement order.

The measurement order generating unit 302 illustrated in FIG. 2 may receive a change in the generated measurement order. The measurement order generating unit 302 may be connected to a reception unit 502 that receives a change in the measurement order from a medical worker. As the reception unit 502, an input device such as a keyboard and a touch panel can be used. Through the reception unit 502, a medical worker may change the measurement items of the measurement order as shown in FIG. 5.

The host computer 300 including the measurement order generating unit 302 is connected to an information processing unit 340 connected to the sample preparation device 30 shown in FIG. 1 via the communication network. The sample preparation device 30 pretreats a specimen to be measured by the flow cytometer included in the sample measuring device 20. The reader included in the sample measuring device 20 reads the identifier of the specimen container and the identifier of the specimen rack. The reader sends the read identifier to the information processing unit 340. The information processing unit 340 queries the host computer 300 via the communication network for the measurement order of the specimen provided with the identifier. The information processing unit 340 sends the measurement order received from the measurement order generating unit 302 to the sample preparation device 30. For example, the sample preparation device 30 pierces a stopper of the specimen container containing the specimen transported by the specimen transport device 40 with a suction tube to aspirate a required amount of specimen from the specimen container. The sample preparation device 30 may stir the specimen in the specimen container before aspirating the specimen.

The sample preparation device 30 dispenses the specimen aspirated from the specimen container into the sample container. The sample preparation device 30 adds a labeling reagent containing an antibody to the specimen in the sample container, based on the measurement order. Thereby, the specimen and the labeling reagent react to form a sample. In the labeling reagent, for example, an antibody such as a monoclonal antibody is labeled with a fluorescent reagent. When the specimen and the labeling reagent react, the sample container may be warmed.

The sample preparation device 30 adds a hemolytic agent into the sample container based on the measurement order, and the sample and the hemolytic agent react. When the sample and the hemolytic agent react, the sample container may be warmed. The hemolytic agent hemolyzes erythrocytes, which are undesirable to be present when analyzing the sample with the flow cytometer included in the sample measuring device 20.

The sample preparation device 30 centrifuges the sample in the sample container, based on the measurement order. After centrifugation, the sample preparation device 30 removes a supernatant from the sample in the sample container. As a result, sediment of the hemolyzed erythrocytes and the labeling reagent which has not bound to the blood cell antigen contained in the supernatant are removed.

The sample preparation device 30 dilutes the sample in the sample container with a buffer, based on the measurement order. The sample preparation device 30 may not seal the sample container containing the prepared sample.

An information processing unit 350 is connected to the sample measuring device 20. The information processing unit 350 sends the measurement order received from the measurement order generating unit 302 included in the host computer 300 to the sample preparation device 30. The flow cytometer included in the sample measuring device 20 may be integrated with the sample preparation device 30. The flow cytometer included in the sample measuring device 20 includes a flow cell. The sample preparation device 30 aspirates the sample in the sample container via a nozzle and a sample flow path. The sample preparation device 30 sends the sample to the flow cell included in the sample measuring device 20. The sample supplied to the flow cell is irradiated with light from a light source, and a light detection unit detects forward scattered light, side scattered light, and fluorescence emitted from the sample. An analysis unit included in the information processing unit 350 is connected to the light detection unit. The analysis unit analyzes the forward scattered light, the side scattered light, and the fluorescence detected by the light detection unit. The analysis unit analyzes the type and antigen characteristic of blood cells contained in the sample.

The sample preparation device 30 and the sample measuring device 20 may not be integrated. In this case, the sample preparation device 30 may hold the sample container containing the prepared sample on a sample container holder such as carousel and rack. The sample container or the sample container holder holding the sample container may be transported from the sample preparation device 30 to the sample measuring device 20 by a medical worker. Alternatively, the sample transport device may transport the sample container or the sample container holder holding the sample container from the sample preparation device 30 to the sample measuring device 20. The sample transport device includes, for example, a conveyor or a robotic arm. Every time a sample is prepared by the sample preparation device 30, a sample container containing the prepared sample may be transported to the sample measuring device 20.

For example, the sample preparation device 30 prepares a plurality of samples and stores the samples in a plurality of sample containers. The plurality of sample containers are held, for example, by one sample container holder. It is preferable that the samples contained in each of the plurality of sample containers held by the sample container holder have a short time interval for preparation. For example, when the sample container is not stoppered, a solvent is more evaporated in the sample prepared earlier and the concentration of the sample is higher than in the sample prepared later, and it may affect the measurement of the sample measuring device 20.

Therefore, the specimen measurement system according to the embodiment may further include a storage unit 70 that stores the specimen container. The storage unit 70 is disposed between the specimen measuring device 10 and the sample preparation device 30, for example, between the smear preparing apparatus 61 and the sample preparation device 30. The storage unit 70 stores the specimen container until the sample preparation device 30 can prepare a plurality of samples from the specimen.

In the sample preparation device 30, when the sample container holder becomes empty, the sample preparation device 30 transmits a signal capable of receiving the specimen to the transport controller 305. The transport controller 305 that has received the signal in which the sample preparation device 30 can receive the specimen controls the storage unit 70, and the storage unit 70 sends out the specimen rack containing the specimen container to the specimen transport device 40. The transport controller 305 controls the specimen transport device 40, and the specimen transport device 40 transports the specimen container from the storage unit 70 to the sample preparation device 30. This shortens the interval of preparation time of each of the plurality of samples held by the sample container holder.

However, when a certain time or more elapses after the blood specimen is collected, the blood specimen may be degraded to affect the measurement of the sample measuring device 20. Therefore, when the storage time exceeds a certain time, the specimen transport device 40 may return the specimen container from the storage unit 70 to the placement unit 50.

The specimen measurement system according to the embodiment may further include a specimen transfer device 80 that transfers the specimen container held in the specimen rack to another specimen rack, according to the destination of the specimen container. The specimen transfer device 80 is disposed, for example, between the smear preparing apparatus 61 and the storage unit 70. For example, when the specimen transport device 40 transports a specimen container from the specimen measuring device 10 or the smear preparing apparatus 61 to the sample preparation device 30, the specimen transfer device 80 does not transfer the specimen container held in the specimen rack to another specimen rack. For example, when the specimen transport device 40 returns the specimen container from the sample preparation device 30 or the storage unit 70 to the placement unit 50, the specimen transfer device 80 transfer the specimen container held in the specimen rack to another specimen rack. However, disposition of the specimen transfer device 80 is optional.

Figure 6:
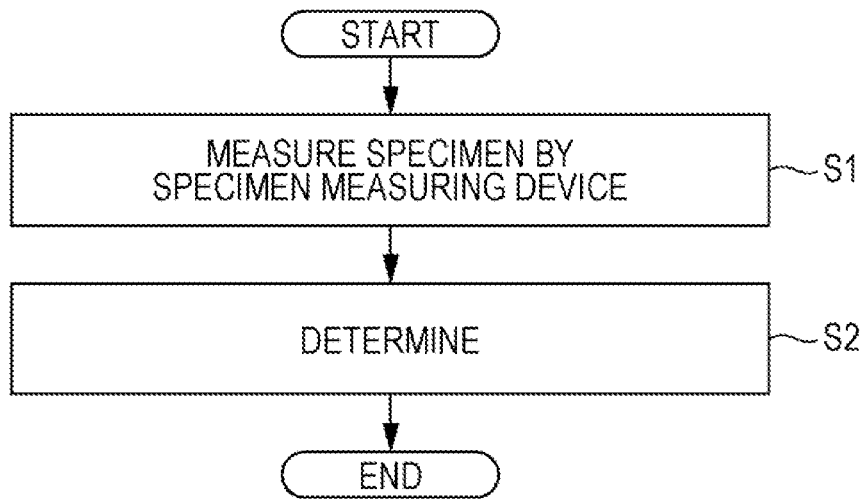
FIG. 6 is a flowchart showing a specimen measurement method according to the embodiment.

Next, the specimen measurement method according to the embodiment will be described with reference to a flowchart shown in FIG. 6. In the specimen measurement method according to the embodiment, step 1 of measuring the specimen by the specimen measuring device 10, and step 2 of determining that whether or not the determination unit 301 measures the specimen by the flow cytometer based on the measurement result of the specimen measuring device 10.

Figure 7:
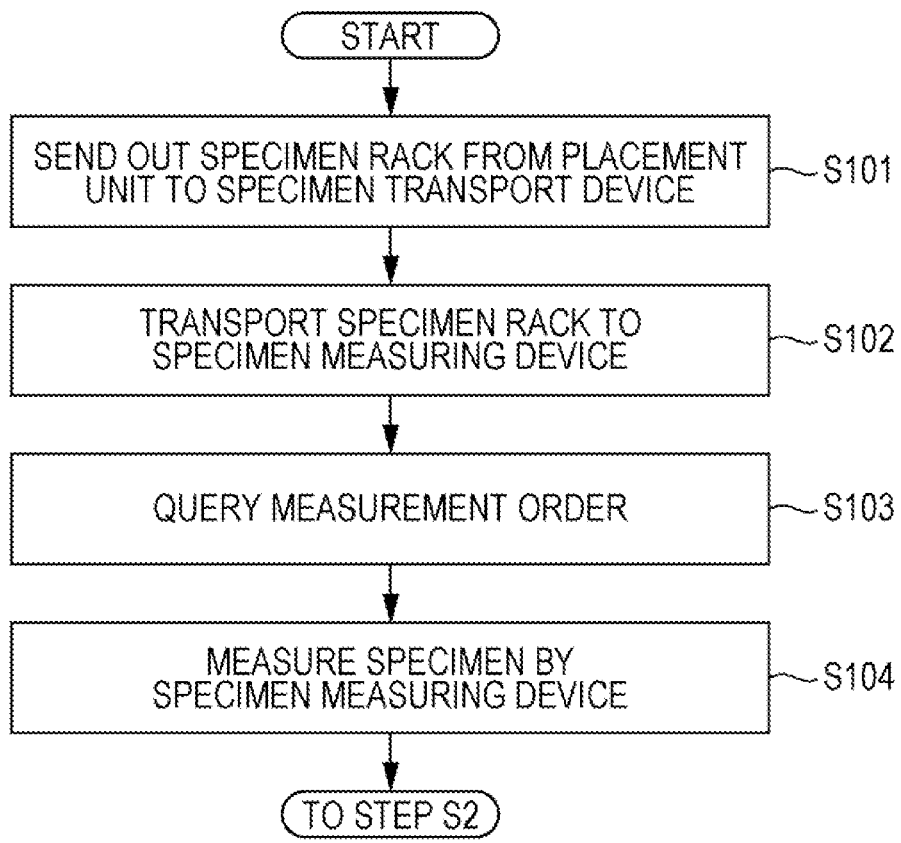
FIG. 7 is a flowchart showing the specimen measurement method according to the embodiment.

Steps included in step 1 of FIG. 6 will be described with reference to a flowchart shown in FIG. 7. In step S101, the specimen rack holding a plurality of specimen containers is placed on the placement unit 50. The reader included in the placement unit 50 reads the identifier of the specimen container and the identifier of the specimen rack. The reader sends the read identifier to a transport controller 305. The transport controller 305 queries the host computer 300 via a communication network whether the received identifier corresponds to a specimen to be examined by any of the plurality of specimen measuring devices 10. When the identifier corresponds to the specimen to be examined by any of the plurality of specimen measuring devices 10, the transport controller 305 controls the placement unit 50, and the placement unit 50 sends out the specimen rack containing the specimen container to the specimen transport device 40.

In step S102, the transport controller 305 controls the specimen transport device 40, and the specimen transport device 40 transports the specimen rack holding the specimen container from the placement unit 50 to the specimen measuring device 10 designated by the host computer 300. In step S103, the reader included in the specimen measuring device 10 to which the specimen rack has been transported reads the identifier of the specimen container and the identifier of the specimen rack, and the information processing unit 310 sends the identifier to the host computer 300. The host computer 300 sends the measurement order prepared in advance for the identifier back to the information processing unit 310. In step S104, the specimen measuring device 10 measures the specimen in accordance with the measurement order received by the information processing unit 310. Thereafter, the process proceeds to step S2 of FIG. 6.

Steps included in step 2 of FIG. 6 will be described with reference to flowcharts shown in FIGS. 8 and 9. In step S201, the determination unit 301 included in the host computer 300 receives the measurement result of the specimen by the specimen measuring device 10 from the information processing unit 310. The determination unit 301 determines whether the specimen meets a predetermined condition, based on the measurement result of the specimen by the specimen measuring device 10. The determination unit 301 determines whether or not the specimen is to be measured by the flow cytometer included in the sample measuring device 20. When it is determined that the specimen meets the predetermined condition and the specimen is to be measured by the flow cytometer, in step S202, the determination unit 301 determines whether the image of the specimen is to be analyzed.

When the determination unit 301 determines that the image is to be analyzed, in step S203, the transport controller 305 controls the specimen transport device 40, and the specimen transport device 40 transports the specimen rack holding the specimen container from the specimen measuring device 10 to the smear preparing apparatus 61. A medical worker may carry the specimen to the smear preparing apparatus 61.

In step S204, the smear preparing apparatus 61 smears the specimen on a transparent substrate. The smear preparing apparatus 61 stains the specimen with a staining solution to prepare a smear preparation. In step S205, the imaging device 62 captures an image of the smear preparation, and the image analysis apparatus 330 analyzes the image of the smear preparation.

In step S206, the determination unit 301 included in the host computer 300 receives the analysis result of the image of the smear preparation from the image analysis apparatus 330. The determination unit 301 determines whether the specimen meets the predetermined condition, based on the measurement result of the specimen by the specimen measuring device 10 and the analysis result of the image of the smear preparation by the image analysis apparatus 330. The determination unit 301 determines whether or not the specimen is to be measured by the flow cytometer included in the sample measuring device 20. When it is determined that the specimen meets the predetermined condition and the specimen is to be measured by the flow cytometer, in step S207, the transport controller 305 queries whether the sample preparation device 30 can receive the specimen. When the sample preparation device 30 can receive the specimen, in step S208, the transport controller 305 controls the specimen transport device 40, and the specimen transport device 40 transports the specimen rack holding the specimen container from the smear preparing apparatus 61 to the sample preparation device 30. A medical worker may carry the specimen to the sample preparation device 30. Thereafter, the process proceeds to step S301 in FIG. 10.

In step S207, when the sample preparation device 30 cannot receive the specimen, in step S241, the transport controller 305 controls the specimen transport device 40 and the storage unit 70, the specimen transport device 40 transports the specimen rack holding the specimen container from the smear preparing apparatus 61 to the storage unit 70, and the storage unit 70 stores the specimen rack. In step S242, in the sample preparation device 30, when the sample container holder becomes empty, the sample preparation device 30 transmits a signal capable of receiving the specimen to the transport controller 305, and the transport controller 305 controls the storage unit 70 and the specimen transport device 40, and the specimen transport device 40 transports the specimen rack holding the specimen container from the storage unit 70 to the sample preparation device 30. Thereafter, the process proceeds to step S301 in FIG. 10.

Figure 8:
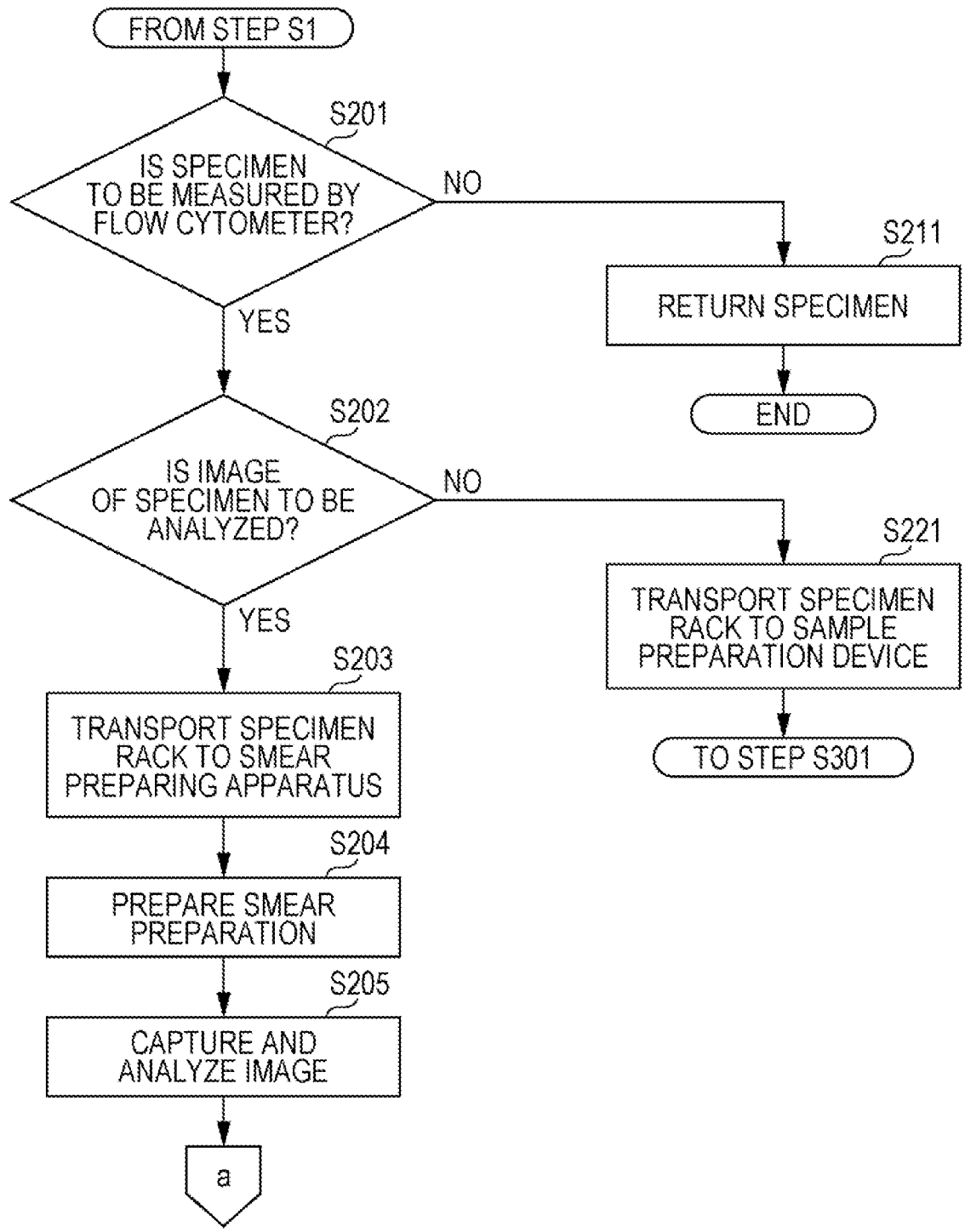
FIG. 8 is a flowchart showing the specimen measurement method according to the embodiment.
Figure 9:
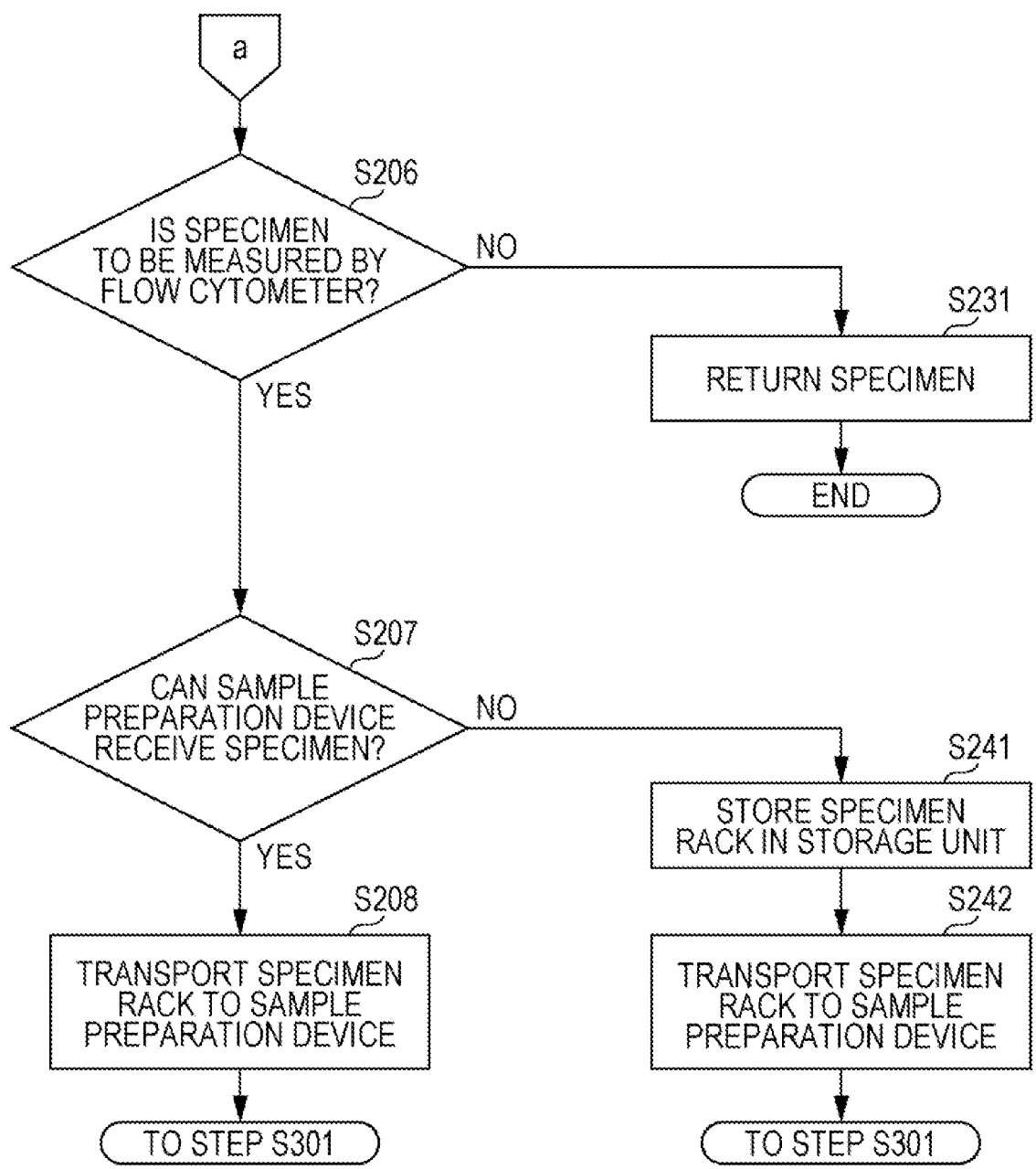
FIG. 9 is a flowchart showing the specimen measurement method according to the embodiment.

When it is determined in step S201 in FIG. 8 that the specimen does not meet the predetermined condition and the specimen is not to be measured by the flow cytometer, in step S211, the transport controller 305 controls the specimen transport device 40, and the specimen transport device 40 returns the specimen rack holding the specimen container from the specimen measuring device 10 to the placement unit 50. A medical worker may remove the specimen from the specimen measuring device 10. When, in step S202, the determination unit 301 determines that the image is not to be analyzed, in step S221, the transport controller 305 controls the specimen transport device 40, and the specimen transport device 40 transports the specimen rack holding the specimen container from the specimen measuring device 10 to the sample preparation device 30. A medical worker may carry the specimen to the sample preparation device 30. The specimen rack may be stored in the storage unit 70 as necessary. Thereafter, the process proceeds to step S301 in FIG. 10. When it is determined in step S206 in FIG. 9 that the specimen does not meet the predetermined condition and the specimen is not to be measured by the flow cytometer, in step S231, the transport controller 305 controls the specimen transport device 40, and the specimen transport device 40 returns the specimen rack holding the specimen container from the smear preparing apparatus 61 to the placement unit 50. A medical worker may remove the specimen from the smear preparing apparatus 61.

Figure 10:
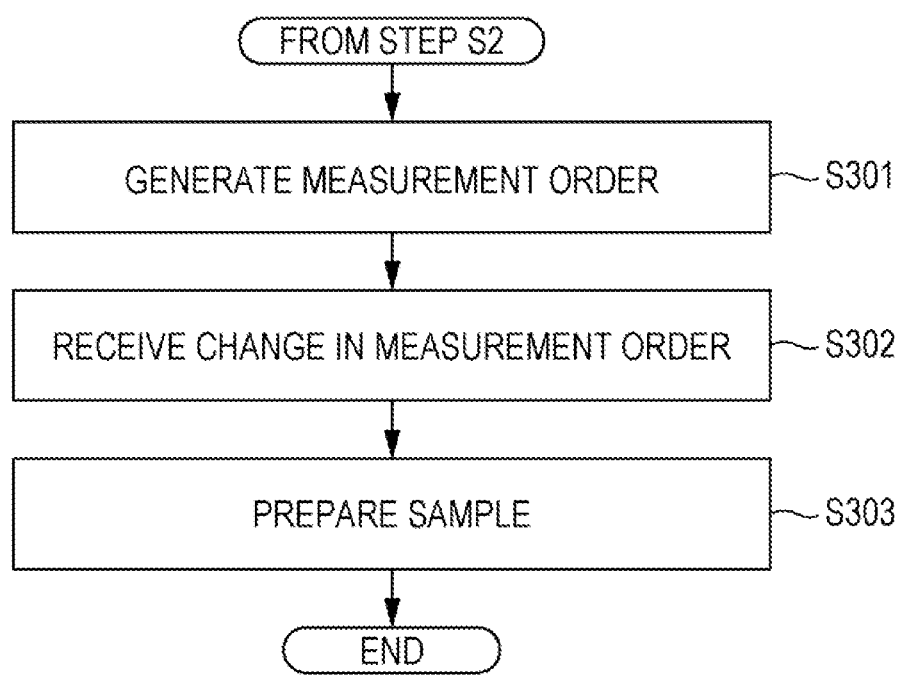
FIG. 10 is a flowchart showing the specimen measurement method according to the embodiment.

In step S301 in FIG. 10, the measurement order generating unit 302 included in the host computer 300 generates a measurement order of the flow cytometer included in the sample measuring device 20, based on at least one of the measurement result by the specimen measuring device 10 and the analysis result of the image of the smear preparation by the image analysis apparatus 330. In step S302, the measurement order generating unit 302 arbitrarily receives a change in the measurement order.

In step S303, the measurement order generating unit 302 sends the measurement order to the information processing unit 340 connected to the sample preparation device 30. The sample preparation device 30 prepares a sample by adding a labeling reagent containing an antibody to the specimen in the sample container, based on the measurement order received by the information processing unit 340. The prepared sample is sent to a sample measuring device 20 including the flow cytometer. The measurement order generating unit 302 sends the measurement order to the information processing unit 350 connected to the sample measuring device 20. The sample measuring device 20 measures the sample, based on the measurement order received by the information processing unit 350.

The embodiment of the invention has been described above; however, it should not be understood that the description and drawings constituting part of this disclosure limit the invention. With this disclosure, various alternative embodiments, examples and operating technologies should be apparent to those skilled in the art. For example, the specimen measurement system according to the embodiment may not include the smear preparing apparatus 61, the imaging device 62, and the image analysis apparatus 330. In this case, the determination unit 301 may determine whether or not the specimen is to be measured by the flow cytometer, based on the measurement result of the specimen by the specimen measuring device 10, without using the result of the image analysis. Alternatively, the determination unit 301 and the measurement order generating unit 302 may receive the analysis result of the image of the smear preparation from the image analysis apparatus outside the specimen measurement system according to the embodiment.

The specimen measuring device 10 is not limited to inclusion of a flow cytometer. For example, when the present disclosure is applied to a test of adult T cell leukemia, it is determined whether the blood specimen is anti-HTLV-I antibody positive, using the specimen measuring device 10 including an immunoanalysis device. When it is positive, the determination unit 301 determines that the specimen is to be measured by the flow cytometer, and the specimen transport device 40 transports the blood specimen to the sample preparation device 30. The sample preparation device 30 prepares a sample from the blood specimen, using a labeling reagent containing, for example, antibodies against CD3, CD4, CD8, and CD45.

The flow cytometer included in the sample measuring device 20 determines whether each of CD3, CD4, CD8, and CD45 in the sample is positive or negative.

The present disclosure is also applicable to tests other than hematopoietic tumor test. For example, when the present disclosure is applied to the test of paroxysmal nocturnal hemoglobinuria (PNH), it is determined whether a urine specimen is positive for bilirubin, using a specimen measuring device 10 including a urine analyzer. When it is positive, the determination unit 301 determines that the specimen is to be measured by the flow cytometer, and the specimen transport device 40 transports the urine specimen to the sample preparation device 30. The sample preparation device 30 prepares a sample from the urine specimen, using a labeling reagent containing, for example, antibodies against CD55 and CD59. The flow cytometer included in the sample measuring device 20 determines whether each of CD55 and CD59 in the sample is positive or negative.

Alternatively, when the present disclosure is applied to the test of ITP, it is determined whether prothrombin time (PT) and activated partial thromboplastin time (APTT) are normal in the blood specimen, using the specimen measuring device 10 further including a blood coagulation analyzer. When the platelet count is equal to or less than the reference value and PT and APTT are normal, the determination unit 301 determines that the specimen is to be measured by the flow cytometer, and the specimen transport device 40 transports the blood specimen to the sample preparation device 30.

The sample preparation device 30 prepares a sample from the blood specimen, using a labeling reagent containing, for example, antibodies against CD36, CD41/61, CD42bc/a/d, CD49b/29, and CD110. The flow cytometer included in the sample measuring device 20 measures whether each of CD36, CD41/61, CD42bc/a/d, CD49b/29 and CD110 in the sample is positive or negative.

For example, when the present disclosure is applied to a test of stem cell transplantation, it is determined whether the leukocyte count in the blood specimen is equal to or more than a reference value, using the specimen measuring device 10 including a blood cell measuring apparatus. When the leukocyte count is equal to or more than the reference value, the determination unit 301 determines that the specimen is to be measured by the flow cytometer, and the specimen transport device 40 transports the blood specimen to the sample preparation device 30. The sample preparation device 30 prepares a sample from the blood specimen, using, for example, a labeling reagent containing an antibody against CD34.

The flow cytometer included in the sample measuring device 20 measures CD34 positive cells in the sample to determine whether CD34 positive cells are present at a predetermined concentration or more.

The configuration of the flow cytometer is not limited to the above. For example, in the flow cell, not only optical information but also electrical parameters such as changes in DC impedance or RF impedance generated when particles in the specimen pass may be measured. As well as measuring forward scattered light and side scattered light to acquire optical information, for example, scattered light at different angles such as low angle scattered light scattering below 10°, low central angle scattered light scattering from 6° to 26° and high central angle scattered light scattering from 15° to 50° may be measured. Further, as optical information, not only scattered light but also optical loss in the axial direction may be measured. It is also possible to classify blood cell types by using these information in combination.

As such, it should be understood that the present disclosure includes various embodiments and the like that are not described herein.

What is claimed is:

1. A specimen measurement system comprising:
a specimen measuring device configured to measure a specimen for a first measurement item;
a flow cytometer configured to measure the specimen for a second measurement item which is different from the first measurement item; and
a determination unit configured to determine whether or not the specimen will be measured by the flow cytometer or by another analysis unit, based on a measurement result of the first measurement item determined by the specimen measuring device.

2. The specimen measurement system according to claim 1, wherein, when the measurement result of the specimen meets a predetermined condition, the determination unit determines that the specimen is to be measured by the flow cytometer.

3. The specimen measurement system according to claim 1, wherein the specimen measuring device includes a flow cytometer separate from the flow cytometer.

4. The specimen measurement system according to claim 3, wherein the specimen measuring device measures the specimen which is not treated with a labeling reagent containing an antibody.

5. The specimen measurement system according to claim 1, wherein
the specimen is a blood specimen,
the specimen measuring device includes a blood cell measuring apparatus that measures blood cells contained in the blood specimen, and
the determination unit determines whether or not the blood specimen is to be measured by the flow cytometer, based on a measurement result of the blood cell measuring apparatus.

6. The specimen measurement system according to claim 5, wherein
the determination unit determines that the blood specimen is to be measured by the flow cytometer when the measurement result of the blood cell measuring apparatus indicates any of: blasts are present, a lymphocyte count meets a predetermined criterion, erythrocyte count meets a predetermined criterion, and platelet count meets a predetermined criterion.

7. The specimen measurement system according to claim 5, further comprising an image analysis apparatus configured to analyze an image of a smear of the blood specimen, wherein
the determination unit determines whether or not the blood specimen is to be measured by the flow cytometer, further based on an analysis result of the image analysis apparatus.

8. The specimen measurement system according to claim 1, wherein
the specimen is a blood specimen,
the specimen measuring device includes an image analysis apparatus configured to analyze an image of a smear of the blood specimen, and
the determination unit determines whether or not the blood specimen is to be measured by the flow cytometer, based on an analysis result of the image analysis apparatus.

9. The specimen measurement system according to claim 7, wherein the image analysis apparatus analyzes whether the image of the smear includes leukemia cells, and
the determination unit determines that the blood specimen is to be measured by the flow cytometer when the analysis result of the image analysis apparatus indicates that the image of the smear includes the leukemia cells.

10. The specimen measurement system according to claim 5, wherein the blood cell measuring apparatus measures another blood specimen which is collected from the same subject at a different time, and
the determination unit determines whether or not the blood specimen is to be measured by the flow cytometer, based on a change between measurement results of the blood specimen and the another blood specimen.

11. The specimen measurement system according to claim 10, wherein the determination unit determines whether or not the blood specimen is to be measured by the flow cytometer, based on a change between blood cell counts of the blood specimen and the another blood specimen.

12. The specimen measurement system according to claim 1, further comprising a measurement order generating unit configured to generate a measurement order for the flow cytometer, based on a measurement result of the specimen measuring device.

13. The specimen measurement system according to claim 12, wherein the measurement order generating unit designates, in the measurement order, a labeling reagent containing an antibody for preparing a sample to be measured by the flow cytometer.

14. The specimen measurement system according to claim 12, further comprising a sample preparation device configured to prepare a sample to be measured by the flow cytometer, at least from a labeling reagent containing an antibody and the specimen, based on the measurement result of the first measurement item by the specimen measuring device.

15. The specimen measurement system according to claim 14, further comprising a specimen transport device configured to transport the specimen to the sample preparation device when the determination unit determines that the specimen is to be measured by the flow cytometer based on the measurement result of the first measurement item by the specimen measuring device.

16. The specimen measurement system according to claim 15, wherein the specimen transport device transports a specimen container containing the specimen.

17. The specimen measurement system according to claim 16, further comprising a storage unit which is disposed between the specimen measuring device and the sample preparation device and is configured to store the specimen container.

18. The specimen measurement system according to claim 17, wherein the storage unit stores the specimen container until the sample preparation device becomes ready to prepare the sample from the specimen.

19. The specimen measurement system according to claim 15, further comprising a sample transport device configured to transport the sample prepared by the sample preparation device to the flow cytometer.

20. A specimen measurement method, comprising:
measuring a specimen by a specimen measuring device for a first measurement item;
determining, by a determination unit, whether or not the specimen is to be measured by a flow cytometer, based on a measurement result of the first measurement item by the specimen measuring device; and
in response to a determination result by the determination unit, measuring the specimen by the flow cytometer for a second measurement item which is different from the first measurement item.

21. The specimen measurement system according to claim 1, wherein the flow cytometer measures the specimen after being treated with a labeling reagent containing an antibody.

22. The specimen measurement system according to claim 1, wherein:
(i) the flow cytometer measures a concentration of CD7, CD11b, CD13, CD14, CD15, CD16, CD33, CD34, CD45, CD56, CD117 and/or HLA-DR positive cells in the specimen;
(ii) a concentration of CD5, CD10, CD19, CD20, CD45, Igκ, Igλ, CD2, CD3, CD4, CD7, CD8 and/or CD56 positive cells in the specimen;
(iii) whether each of CD3, CD4, CD8, and CD45 in the specimen is positive or negative;
(iv) whether each of CD55 and CD59 in the specimen is positive or negative; or (v) whether each of CD36, CD41/61, CD42bc/a/d, CD49b/29 and CD110 in the specimen is positive or negative.

* * * * *